United States Patent [19]

Higuchi et al.

[11] 4,178,376
[45] Dec. 11, 1979

[54] METHOD FOR INDUCING RAPID THERAPEUTICALLY EFFECTIVE ANTIMALARIAL LEVELS OF CERTAIN SELECTED CONVENTIONAL ANTIMALARIALS

[75] Inventors: Takeru Higuchi; Siegfried Lindenbaum, both of Lawrence, Kans.

[73] Assignee: Interx Research Corporation, Lawrence, Kans.

[21] Appl. No.: 760,859

[22] Filed: Jan. 21, 1977

[51] Int. Cl.$^2$ .................... A61K 31/47; A61K 9/42; A61K 31/44; A61K 31/135
[52] U.S. Cl. ........................... 424/258; 424/38; 424/263; 424/330
[58] Field of Search .............................. 424/258, 38,

[56] References Cited
U.S. PATENT DOCUMENTS 3,082,154   3/1963   Allan .................................... 424/38

OTHER PUBLICATIONS

Chemical Abstracts 79:406t (1973)

*Primary Examiner*—Jerome D. Goldberg

[57] ABSTRACT

Rapid therapeutically effective antimalarial levels of a member selected from the group consisting of 6,8-Dichloro-α-(dibutyl-amino-methyl-2-(3',4'-dichlorophenyl-4-quinolinemethanol, 3-Dibutylamino-1-[2,6-bis(4-trifluoromethylphenyl)-4-pyridyl]propanol and 1,3-Dichloro-6-trifluoromethyl-9-[1-hydroxy-3-(dibutylamino) propyl]-phenanthrene are achieved by dissolving the same in an organic fatty acid of the formula: R-CCOH, wherein R represents a member selected from the group consisting of a saturated aliphatic hydrocarbon group of from seven to twenty carbon atoms and a mono-, di-, tri-, or tetra-unsaturated hydrocarbon group of from seven to twenty carbon atoms, and subsequently administering said acid containing the dissolved compound to a warm-blooded animal (e.g., human) afflicted with malaria.

Because of the extremely poor solubility of the above-described antimalarial compounds, therapeutically effective antimalarial blood levels of the same have only been able to be achieved when such compounds are administered around the clock for extended periods of time. The method of this invention substantially enhances the bioavailability of these compounds and thus permits rapid therapeutically effective antimalarial blood levels of the same to be achieved.

10 Claims, No Drawings

METHOD FOR INDUCING RAPID THERAPEUTICALLY EFFECTIVE ANTIMALARIAL LEVELS OF CERTAIN SELECTED CONVENTIONAL ANTIMALARIALS

This application and the invention described herein was made in the course of a contract under the U.S. Army Medical and Development Command Department of the United States Army.

BACKGROUND OF THE INVENTION

1. Field of the Invention

The present invention is directed to certain selected conventional antimalarial compounds, and more particularly, the present invention is directed to a method for substantially increasing the bioavailability of the same so as to permit rapid therapeutically effective antimalarial blood levels of the same to be achieved.

2. Description of the Prior Art 6-8-Dichloro-α-(dibutylaminomethyl-2-(3',4'-dichlorophenyl)-4-quinolinemethanol, 3-Dibutylamino-1-[2,6-bis(4-trifluoromethylphenyl)-4-pyridyl] propanol and 1,3-Dichloro-6-trifluoromethyl-9-[1-hydroxy-3-(dibutylamino) propyl]-phenanthrene are well known compounds somewhat useful in the treatment of malaria in warm-blooded animals, e.g., humans. For instance, see, R. E. Lutz, et al, *J. Amer. Chem. Soc.*, 68, 1813 (1946), P. Blumbergs, et al, *J. Med. Chem.*, 15, No. 8, 808 (1972), and W. T. Colwell, et al, *J. Med. Chem.*, 15, No. 7, 771 (1972).

Unfortunately, because of the extremely poor solubility of these compounds therapeutically effective antimalarial blood levels of the same can only be achieved when administering the same around the clock for an extended period of time. For example, the aqueous solubility of 6,6-Dichloro-α-(dibutylaminomethyl-2-(3',4'-Dichlorophenyl)-4-quinolinemethanol is approximately 1.0 mg per liter of water whereas the solubility of 3-Dibutylamino-1-[2,6-bis(4-trifluoromethylphenyl)-4-pyridyl] propanol is approximately 7.0 mg per liter of water, respectively. As can be seen, due to this extremely poor solubility, massive doses of these compounds must be administered before any therapeutically effective blood levels of the same can be achieved.

For a number of years, numerous investigators have attempted a myriad of structural modifications to these compounds in the hope of increasing their solubility which in turn would increase the bioavailability of the same (the ability of the compound to achieve a rapid therapeutically effective antimalarial blood level). However, all attempts have met with little, if any, success. Similarly, investigators have also attempted to pharmaceutically formulate these compounds in such a manner as to increase the solubility of the same, and hence, the bioavailability thereof. However, again, little, if any, success has been observed.

Consequently, it is apparent that a great need exists for a means to formulate the above-identified compounds to the extent that (1) a rapid therapeutically effective antimalarial blood level of the same can be achieved without (2) increased toxicity.

SUMMARY OF THE INVENTION

It is the primary object of the present invention to provide a means for substantially enhancing the bioavailability of the above-identified compounds.

It is another object of the present invention to achieve rapid therapeutically effective antimalarial blood levels of the above-described compounds without introducing solubilizing agents which themselves contribute to the toxicity.

These and other objects not heretofore described are achieved by dissolving a member selected from the group consisting of 6,8-Dichloro-α-(dibutylaminomethyl-2-(3',4'-dichlorophenyl)-4-quinolinemethanol, 3-Dibutylamino-1-[2,6-bis(4-trifluoromethylphenyl)-4-pyridyl] propanol, and 1,3-dichloro-6-trifluoromethyl-9-[1-hydroxy-3-(dibutylamino) propyl]-phenanthrene in an organic fatty acid of the formula: R—COOH, wherein R represents a member selected from the group consisting of a saturated aliphatic hydrocarbon group of from seven to twenty carbon atoms and a mono-, di-, tri-, or tetra-unsaturated hydrocarbon group of from seven to twenty carbon atoms, and, subsequently, administering the resulting composition to a warm-blooded animal, e.g., a human afflicted with malaria.

With reference to the organic fatty acid employed, any one of those acids encompassed within applicant's generic formula is operable. For instance, without limitation, heptanoic, octanoic, nonanoic, decanoic, lauric, myristic, pentadecanoic, palmitic, margaric, stearic, myristoleic, palmitoleic, oleic, linoleic, linolenic, and arachidonic acid are all operable. However, exceptional results have been obtained with nonanoic acid, oleic acid and stearic acid, respectively.

As for the formulation, per se, the amount of organic fatty acid required to solubilize the particular antimalarial compound chosen is not at all critical. However, normally, 4.0 mg of fatty acid is employed per 1.0 mg of antimalarial compound. This range is not to be considered limitative, as solubilization can be achieved by employing amounts outside of the aforementioned range as well.

The above-described composition can be administered to a warm-blooded animal by any orally acceptable means such as in teaspoonful doses, hard capsules or tablets, provided the patient receives a therapeutic dose of the antimalarial compound employed and depending upon the physical state of the final formulation, e.g., liquid or solid. For example, the therapeutic dose for dichloro-α-(dibutylaminomethyl-2-(3',4'-dichlorophenyl)-4-quinolinemethanol is 230 mg. Optionally, the composition can be flavored to overcome taste impediments or the composition can be administered via a "soft" gelatin capsule. Soft gelatin capsules can be obtained from Banner Gelatin Products, Incorporated of Chatsworth, CA.

Without further elaboration, it is believed that one of ordinary skill in the art can, using the preceding description, utilize the present invention to its fullest extent. Accordingly, the following preferred specific embodiments are, therefore, to be construed as merely illustrative, and not limitative of the remainder of the specification and claims in any way whatsoever.

EXAMPLE I

Summary of the Pharmacokinetic Parameters of Two Different Dosage Forms of 6,8-Dichloro-α-(Dibutylaminomethyl-2-(3',4'-Dichlorophenyl)-4-Quinolinemethanol In order to demonstrate the uniqueness of the invention disclosed herein, in vivo studies were carried out with two different dosage forms of the above-identified compound, one dosage form being that of a conventional pharmaceutically acceptable capsule containing the above-described compound and the other dosage form being a "soft" gelatin capsule containing the above-described compound dissolved in oleic acid. The actual composition of each capsule employed is set out below. For the sake of convenience, the compound 6,8-Dichloro-α-(dibutylaminomethyl-2-(3',4'-dichlorophenyl)-4-quinolinemethanol is noted as "Compound I".

| STANDARD GELATIN CAPSULE: | | SOFT GELATIN CAPSULE (THIS INVENTION): | |
|---|---|---|---|
| Compound I* | 250 mg | Compound I | 78 mg |
| Sterotex | 17 mg | Oleic Acid | 312 mg |
| Talc | 56 mg | | 390 mg |
| Cab-O-Sil | 17 mg | | |
| | 340 mg | | |

*HCl salt

BIOAVAILABILITY EXPERIMENTS IN BEAGLE DOGS

Four female Beagle dogs were chosen for the experiment. Each dog was to receive two different dosage forms of Compound I. A 250 mg conventional capsule as provided above and 234 mg of Compound I (free base) equivalent to 250 mg of the HCl salt thereof in oleic acid (20% of Compound I, free base by weight) were given in three hand-filled "soft" gelatin capsules as provided above.

The dogs were fasted 18 hours prior to the experiment. After administration of the capsules, 200 ml of water was given through a tube inserted into the stomach.

Table I set out below shows the blood levels of Compound I measured at various times for each of the formulations. The first four dogs listed are females; and IX 51, a male dog, tested in a preliminary experiment, is also included in this Table which summarizes some of the most important parameters.

TABLE I
SUMMARY OF PHARMACOKINETIC PARAMETERS FOR TWO DIFFERENT DOSAGE FORMS OF COMPOUND I

| Dog No. | Body Weight Kg. | Dose[a] mg/kg | Peak Concn. μg/ml. | Time Peak Concn. Hour | AUC[b] μg.Hr.ml$^{-1}$ | AUC[c] Corrected for Dose |
|---|---|---|---|---|---|---|
| STANDARD GELATIN CAPSULE | | | | | | |
| IX-15 | 15.6 | 6.1 | 0.298 | 4.0 | 0.908 | 0.056 |
| IX-16 | 12.4 | 20.1 | 0.778 | 3.0 | 2.487 | 0.124 |
| IX-17 | 13.8 | 18.1 | 4.584 | 3.0 | 16.212 | 0.896[d] |
| IX-18 | 16.2 | 15.4 | 0.632 | 4.0 | 1.056 | 0.069 |
| IX-51 | 10.0 | 25.0 | 0.740 | 3.0 | 1.375 | 0.055 |
| SOFT GELATIN CAPSULE (THIS INVENTION) | | | | | | |
| IX-15 | 14.0 | 18.0 | 2.842 | 2.0 | 8.773 | 0.487 |
| IX-16 | 11.8 | 21.1 | 4.139 | 3.0 | 12.184 | 0.577 |
| IX-17 | 14.0 | 23.8 | 4.880 | 3.0 | 16.492 | 0.693 |
| IX-18 | 15.5 | 16.1 | 6.781 | 5.0 | 17.677 | 1.098 |
| IX-51 | 10.5 | 21.9 | 2.552 | 2.0 | 5.101 | 0.233 |

[a]Calcd. as WR-30,090 (hydrochloride)
[b]Area under the curve calcd. by the trapezoidal method.
[c]Column 6 divided by Column 3 of this table.
[d]Value eliminated in calculation of average value.

EXTRACTION PROCEDURE

A 10 ml plastic disposable syringe was used to remove 5 ml of blood from each dog tested. The blood was immediately discharged into a 15 ml glass centrifuged tube of the screw-cap type having a polyethylene or teflon seal. The blood was mixed with two drops of 15% EDTA solution previously added to the centrifuged tube. 5 ml of reagent grade ether were then added, and the cap was screwed down tightly. The centrifuge tube was shaken vigorously on a wrist-action shaker with modified, 7-inch long rocker arms to hold the centrifuge tubes in a horizontal position. After one hour of continuous shaking, the tubes were removed and centrifuged on a small clinical centrifuge for ten minutes at approximately 5000×g. The centrifuge tubes were then immersed in a dry ice acetone bath to freeze the aqueous layer. The ether layer, about 4 ml, was decanted into a 15 ml conical-shaped glass centrifuge tube. The extraction procedure was repeated using the same procedure. The ether layer from the second extraction (about 5 ml) was then added to the ether layer from the first extraction, and both were evaporated to about one-third the total volume using a rotary Evapo-mix (test tube model) at room temperature. The extraction procedure was repeated a third time, and the ether layer (5 ml) was added to the ether layer from the previous extraction steps. Evaporation of the ether was done on a rotary Evapo-mix until only a small amount of liquid, about 0.5 ml was left in each tube. The remaining solvent was evaporated under vacuum one tube at a time, by tipping the tube nearly horizontal to prevent bumping. The centrifuge tubes were placed in a vacuum desiccator containing calcium chloride, and the contents were completely dried overnight under vacuum in the dark. The solid material was dissolved, just prior to analysis, with 100 μl of a 20% chloroform−80% heptane solution (all chemicals used were standard reagent grade). Usually 10 μl of this solution was injected on the HPLC column, but for high concentrations of Compound I, free base (greater than 2 μg/ml), a 5 μl sample or a further dilution of the solid material was employed.

The recovery of Compound I from spiked blood samples was determined using this extraction procedure. Table II shows some data for samples spiked with Compound I, shaken for one hour to allow equilibration and then extracted. The recovery is 80% for samples of 200 ng or larger, with a range of about 6% for samples of relatively high concentration. A larger variability was observed with spike samples in the 50–200 ng/ml range. The cause of this variability in the low range is probably due to the column condition of the liquid chromatograph rather than the extraction procedure.

TABLE II
RECOVERY PERCENTAGES OF SPIKED BLOOD SAMPLES OF COMPOUND I (FREE BASE)

| Spiked Concentration | Percent Recovery[a] | |
|---|---|---|
| μg/ml of blood | Column 1[b] | Column 2[c] |
| 0.05 | 52 | 98 |
| 0.20 | 75 | 87 |
| 0.50 | 75 | 82 |
| 1.0 | 87 | 77 |
| 3.0 | 85 | 79 |

[a]Single runs on spiked blood samples.
[b]Corasil Type II column using 20% dioxane-heptane as mobile phase.
[c]Corasil Type II column using 3%–10% methanol in 20% dioxane-heptane mixture as mobile phase.

HIGH PRESSURE LIQUID CHROMATOGRAPHIC ANALYSIS

A varian model 4000 high-pressure liquid chromatograph equipped with a uv absorption detector at 280 mm was used in the analysis. Corasil Type II packing material is the stationary phase. The column used was a 1.8 mm stainless steel column, 50 cm in length, hand-filled by tapping on a solid support using a wrist-action shaker. A system was developed in which one column could be used for approximately 40 injections after which the mobile phase needs to be changed slightly to retain good peak separation. A standard concentration of Compound I, free base and 20% chloroform-heptane was injected before and after each blood sample. The average area of the standard peaks was used to define the column sensitivity for that particular run. The mobile phase used with a fresh Corasil Type II column is 10% methanol by volume in the stock solvent (20% dioxane-heptane, v/v). The mobile phase was dried over anhydrous sodium sulfate and then degassed in order to achieve reproducible results. As the column was used, the separation of Compound I (free base) from the blood components worsened, and the amount of methanol had to be decreased to give good separation. A column is used until the methanol concentration must be decreased to less than 3% to give a good separation. A new column changes its retention time for the compound as extracted blood samples are injected; therefore, a new column receives about ten injections of blood samples and is allowed to sit overnight before use. After blood samples have been injected in this manner, the column is stable for many injections.

SUMMARY ON BIOAVAILABILITY

In determining the increased bioavailability of the oleic acid formulation as compared to the standard capsule formation, the values for the corrected area under the curve (column labelled "AUC Corrected for Dose") were used. The value of 0.896 for dog IX-17 was eliminated from the average of the area under the curve for the standard capsule, since its deviation is eleven times the average deviation of the remaining observations from their mean. The average corrected values for the area under the curve are 0.076 and 0.618 for the standard capsule and oleic acid formulation, respectively. This gives an 8.1 times larger area under the curve for the oleic acid formulation as compared to that of the standard capsule formulation.

From the foregoing description, one of ordinary skill in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

What we claim is:

1. A method for inducing rapid therapeutically effective blood levels of 6,8-Dichloro-$\alpha$-(dibutylaminomethyl-2-(3′,4′-dichlorophenyl)-4-quinolinemethanol, in a warm-blooded animal afflicted with malaria which comprises administering to said animal a composition consisting essentially of:
   (a) an effective antimalarial amount of 6,8-Dichloro-$\alpha$-(dibutylaminomethyl-2-(3′,4′-dichlorophenyl)-4-quinolinemethanol, dissolved in,
   (b) a solubilizing amount of an organic fatty acid of the formula: R—COOH, wherein R represents a member selected from the group consisting of a saturated aliphatic hydrocarbon group of from seven to twenty carbon atoms and a mono-, di-, tri-, or tetra-unsaturated aliphatic hydrocarbon group of from seven to twenty carbon atoms.

2. The method of claim 1, wherein said organic fatty acid is a member selected from the group consisting of heptanoic acid, octanoic acid, nonanoic acid, decanoic acid, lauric acid, myristic acid, pentadecanoic acid, palmitic acid, margaric acid, stearic acid, myristoleic acid, palmitoleic acid, oleic acid, linoleic acid, linolenic acid and arachidonic acid.

3. The method of claim 2, wherein said acid is a member selected from the group consisting of nonanoic acid, oleic acid and stearic acid.

4. The method of claim 1, wherein said composition is orally administered via a soft or hard gelatin capsule.

5. The method of claim 1, wherein said acid is present in an amount of 4 mg. per 1 mg. of said compound.

6. A pharmaceutical composition consisting essentially of:
   (a) an effective antimalarial amount of 6,8-dichloro-$\alpha$-(dibutylaminomethyl-2-(3′,4′-dichlorophenyl)-4-quinolinemethanol, dissolved in,
   (b) a solubilizing amount of an organic fatty acid of the formula: R—COOH, wherein R represents a member selected from the group consisting of a saturated aliphatic hydrocarbon group of from seven to twenty carbon atoms and a mono-, di-, tri-, or tetra-unsaturated aliphatic hydrocarbon group of from seven to twenty carbon atoms.

7. The composition of claim 6, wherein said organic fatty acid is a member selected from the group consisting of heptanoic acid, octanoic acid, nonanoic acid, decanoic acid, lauric acid, myristic acid, pentadecanoic acid, palmitic acid, margaric acid, stearic acid, myristoleic acid, palmitoleic acid, oleic acid, linoleic acid, linolenic acid and arachidonic acid.

8. The composition of claim 7, wherein said acid is a member selected from the group consisting of nonanoic acid, oleic acid and stearic acid.

9. The composition of claim 6, wherein said composition is orally administered via a soft or hard gelatin capsule.

10. The composition of claim 6, wherein said acid is present in an amount of 4 mg. per 1 mg. of said compound.

* * * * *